United States Patent [19]
Yoder, Jr.

[11] Patent Number: 5,219,344
[45] Date of Patent: Jun. 15, 1993

[54] METHODS AND APPARATUS FOR LASER SCULPTURE OF THE CORNEA

[75] Inventor: Paul R. Yoder, Jr., Wilton, Conn.

[73] Assignee: VISX, Incorporated, Santa Clara, Calif.

[21] Appl. No.: 735,294

[22] Filed: Jul. 24, 1991

Related U.S. Application Data

[63] Continuation of Ser. No. 397,111, Aug. 22, 1989, abandoned, which is a continuation-in-part of Ser. No. 350,444, May 11, 1989, abandoned, which is a continuation-in-part of Ser. No. 314,654, Feb. 23, 1989, abandoned, which is a continuation-in-part of Ser. No. 204,504, Jun. 9, 1988, abandoned.

[51] Int. Cl.$^5$ .............................................. A61N 5/06
[52] U.S. Cl. .......................................... 606/5; 606/3; 606/10; 606/13; 128/848
[58] Field of Search ............... 128/395, 397, 398, 897, 128/898; 606/2-6, 10-19

[56] References Cited
FOREIGN PATENT DOCUMENTS
218427  4/1987  European Pat. Off. ................. 606/5

Primary Examiner—David M. Shay
Attorney, Agent, or Firm—Hopgood, Calimafde, Kalil, Blaustein & Judlowe

[57] ABSTRACT

In use of laser radiation to ablate corneal tissue, to achieve a sculptured change in curvature of the optically used region of the cornea, a variable magnification (zoom) lens is combined with different sized apertures of an indexible mask to develop a relatively smooth profile for the changed curvature. The zoom-lens settings are varied in the course of cornea exposure through each of the succession of mask apertures. To do this, the range of zoom-lens magnification can always be less than 2:1, yet the zoom-lens system can effectively reduce to insignificance the stepped profiling that is inherent in reliance only upon the indexed aperture technique. Also described are techniques to achieve compensation for delivered flux-density variation as a function of instantaneous zoom-lens setting, and programmable control of the area of delivered flux density in a manner to correct for parabolic or other fall-off in delivered beam intensity as a function of radius outward of the axis of beam delivery.

40 Claims, 7 Drawing Sheets

FIG. 5.

ANNULAR MASK AND ABLATION DIAMETERS
FOR 8-ZONE HYPEROPIA CORRECTION

| MASK NO. | MASK DIAM. (mm) INNER | OUTER | ABLATION DIAM. (mm)* INNER | OUTER |
|---|---|---|---|---|
| 1 | 3.255 | 25.000 | 0.911 | 7.000 |
| 2 | 6.585 | 24.111 | 1.844 | 6.751 |
| 3 | 9.255 | 23.220 | 2.591 | 6.502 |
| 4 | 11.266 | 22.330 | 3.154 | 6.252 |
| 5 | 12.930 | 21.438 | 3.620 | 6.003 |
| 6 | 14.370 | 20.545 | 4.024 | 5.753 |
| 7 | 15.648 | 19.652 | 4.381 | 5.503 |
| 8 | 16.802 | 18.758 | 4.705 | 5.252 |

\* Based on constant magnification of 0.2800
all step heights = 0.0102 mm.

FIG. 5A.

MASK AND IRIS DIMENSIONS REQUIRED TO EXPAND
HYPEROPIA CORRECTION TO 3N-2=22 ZONES

| ZONE NO. | MASK DIAM. (mm) INNER | OUTER | IRIS DIAM. (mm) | MAGNI- FICATION | RESULTING ABLATION DIAM. (mm)* INNER | OUTER |
|---|---|---|---|---|---|---|
| 1 | 3.255 | 25.000 | 25.000 | 0.2800 | 0.911 | 7.000 |
|  |  |  | 18.422 | 0.3755 | 1.222 | 6.917 |
|  |  |  | 14.511 | 0.4709 | 1.533 | 6.834 |
| 2 | 6.585 | 25.000 | 24.116 | 0.2800 | 1.844 | 6.751 |
|  |  |  | 20.978 | 0.3178 | 2.093 | 6.668 |
|  |  |  | 18.513 | 0.3557 | 2.342 | 6.585 |
| 3 | 9.255 | 25.000 | 23.220 | 0.2800 | 2.591 | 6.502 |
|  |  |  | 21.376 | 0.3003 | 2.779 | 6.419 |
|  |  |  | 19.764 | 0.3206 | 2.967 | 6.335 |
| 4 | 11.266 | 25.000 | 22.330 | 0.2800 | 3.154 | 6.252 |
|  |  |  | 20.998 | 0.2938 | 3.310 | 6.169 |
|  |  |  | 19.787 | 0.3076 | 3.465 | 6.086 |
| 5 | 12.930 | 25.000 | 21.438 | 0.2800 | 3.620 | 6.003 |
|  |  |  | 20.384 | 0.2904 | 3.755 | 5.919 |
|  |  |  | 19.403 | 0.3008 | 3.889 | 5.836 |
| 6 | 14.370 | 25.000 | 20.545 | 0.2800 | 4.024 | 5.753 |
|  |  |  | 19.664 | 0.2883 | 4.143 | 5.669 |
|  |  |  | 18.833 | 0.2966 | 4.262 | 5.586 |
| 7 | 15.648 | 25.000 | 19.652 | 0.2800 | 4.381 | 5.503 |
|  |  |  | 18.889 | 0.2869 | 4.489 | 5.419 |
|  |  |  | 18.163 | 0.2938 | 4.597 | 5.336 |
| 8 | 16.802 | 25.000 | 18.758 | 0.2800 | 4.705 | 5.252 |

\* NOTE: All step heights = 0.0034 mm.

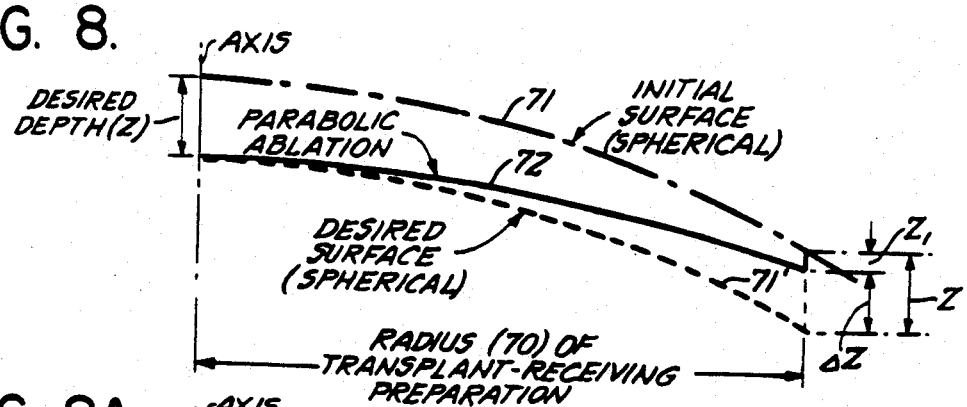
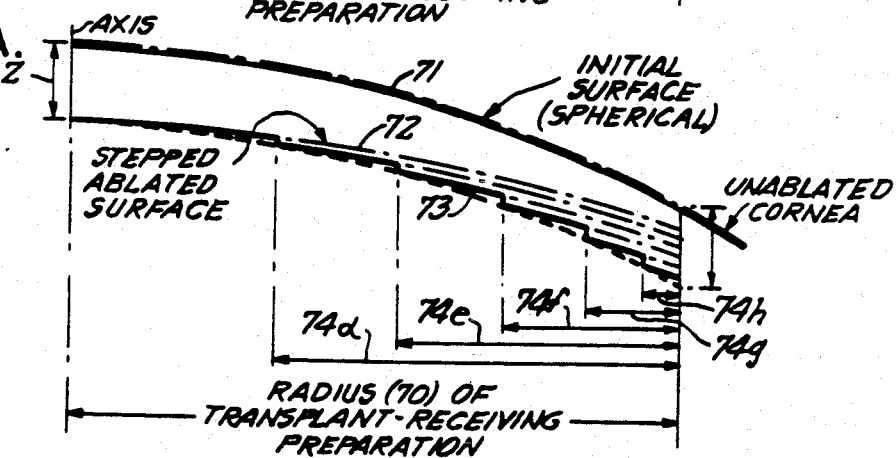
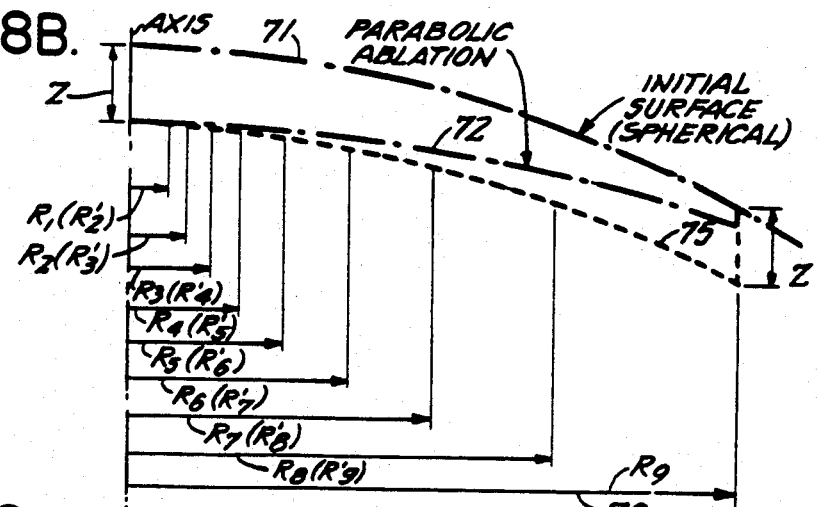
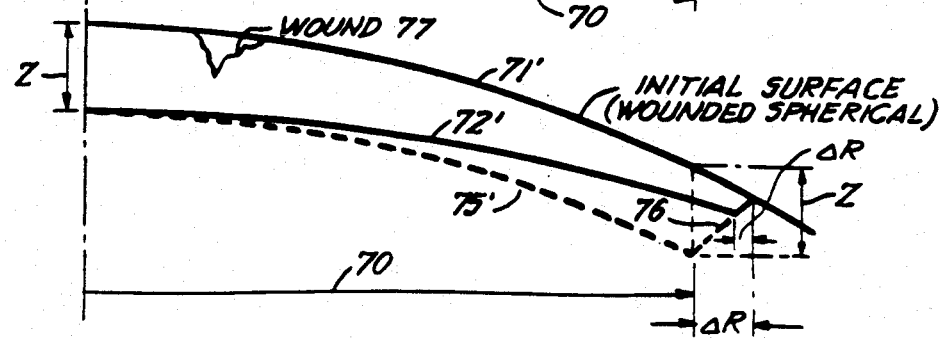

METHODS AND APPARATUS FOR LASER SCULPTURE OF THE CORNEA

RELATED CASES

This application is a continuation of pending application Ser. No. 07/397,111, filed Aug. 22, 1989, now abandoned which is a continuation-in-part of copending application Ser. No. 07/350,444, filed May 11, 1989, now abandoned and said copending application is the second of two prior continuation-in-part applications; the first of said two prior which are continuation-in-part applications, namely, Serial No. 314,654, filed Feb. 23, 1989, now abandoned is a continuation-in-part of original application Serial No. 07/204,504, filed Jun, 9, 1988 now abandoned.

BACKGROUND OF THE INVENTION

The invention relates to that aspect of ophthalmic surgery which is concerned with operations upon the external surface of the cornea.

L'Esperance, Jr. U.S. Pat. Nos. 4,729,372 and 4,732,148 describe methods and apparatus for selective and progressive laser ablation of corneal tissue whereby to sculpt a new optically corrected curvature in the optically used portion of the anterior surface of the cornea. Specific illustrations are given for effecting such optically correcting change, in the cases of myopia, hyperopia and astigmatism. The involved principles are applicable for any ablation-producing wavelength, but the specific illustrative disclosure is for use of ultraviolet radiation, in the range of 200 nanometers or less. Reference is made to said patents and to the patent applications referred to therein, for a more complete discussion of tissue ablation and of various techniques for effecting desired corneal-curvature changes.

It suffices for present purposes to explain that the techniques disclosed in said patents may be generically described as employing varying laser-spot size at impingement with the cornea, in the course of a single surgical procedure. According to one mode, a zoom lens is the means of progressive variation of spot size; if the spot is circular and of progressively varying radius, ablation is greater on the optical axis of the eye, and ablation reduces with increasing radius, thus providing a myopia-correcting curvature change in the anterior surface of the cornea. According to another mode, an indexible mask has a progressive development of apertures of varying size which, for the case of myopia correction, are circular and of progressively varying radius.

Each of these modes is subject to at least one limitation which is believed to prevent realization of optimum results. In the case of zoom-lens reliance for spot-size variation, the desired range of spot-size variation can be as much as 5:1 or 10:1, but the greater the magnification range of a zoom-lens system, the greater the range of laser-beam flux density deliverable to the cornea, i.e., flux-density reduction as a function of increasing magnification. In the case of an indexed-aperture mask, the ablated ultimate new curvature is in reality a series of stepped penetrations which only approximate a smooth curvature.

What has been said, as to use of said patents for tissue-ablating laser surgery to reduce myopia, applies also (1) for varying annular-spot projections to reduce hyperopia and (2) for varying slit-width projections to reduce astigmatism.

BRIEF STATEMENT OF THE INVENTION

It is an object of the invention to provide improved sculpturing apparatus and techniques for surgically operating upon the outer surface of the cornea.

It is a specific object to meet the above object while achieving a materially smoother reprofiling of the optically used region of the cornea.

Another specific object is to achieve the above objects with relatively little change from structure disclosed in said L'Esperance, Jr. patents.

A further specific object is to realize the above objects with minimum change in laser-beam flux density at the cornea, throughout a given curvature-changing surgical procedure; stated in other words, it is also an object to achieve the above object with substantially constant flux-density delivery to the cornea, throughout a given such procedure.

Yet another object is to define a means of achieving this smoother profile in myopia, hyperopia and astigmatic type corrections of the human eye.

Still further, it is a specific object to provide a method and means for effectively removing a wound in the anterior surface of the cornea, with or without net curvature change, as may be required for the particular patient's eye.

A general object is to achieve the above objects with enhanced quality of optical result and with relatively little added hardware complexity (which may detract from reliability and/or maintainability) or cost.

The invention achieves these objects by combining the varying spot-size capabilities of a variable magnification (zoom) lens with those of an indexible mask having a progression of variously sized apertures, designed as appropriate for the particular curvature-reducing or curvature-increasing sculpture that is prescribed for a given patient's optical-curvature problem. The zoom-lens settings are varied in the course of cornea exposure through each of the succession of mask apertures. To do this, the range of zoom-lens magnification can always be less than 2:1, yet the zoom-lens system can effectively reduce to insignificance the stepped profiling that is inherent in reliance only upon the indexed aperture technique. And, for maintenance of substantially constant delivered laser flux density, the output beam of the laser is attenuated in inverse relation to the instantaneous magnification of the zoom system.

Still further, for situations in which a Gaussian profile characterizes the effective distribution of flux density across the operative section of the ablating laser beam, the invention provides for such cooperative use of a suitable indexible mask, zoom-lens system and laser-beam attenuator as to produce not only desired optical-curvature corrections but also sculpture in depth to reproduce original curvature, as for the acceptance of a corneal transplant, or for the removal of a scar or other anterior-surface damage to the cornea.

DETAILED DESCRIPTION

The invention will be described in detail for a preferred embodiment, in conjunction with the accompanying drawings, in which:

FIG. 5 is a table of mask-opening diameters applicable to an illustrative use of FIG. 2;

FIG. 5A is a table of mask-opening diameters, iris settings, and zoom-lens settings for achieving the improvement of the invention, using apparatus of FIGS. 1 and 2A;

FIGS. 8, 8A and 8B are similar diagrams in the style of FIG. 2, to illustrate preparation for a corneal transplant;

FIG. 9 is another diagram in the style of FIG. 2, to illustrate use of the invention to eliminate the effect of scar damage to the cornea.

Figure 1:
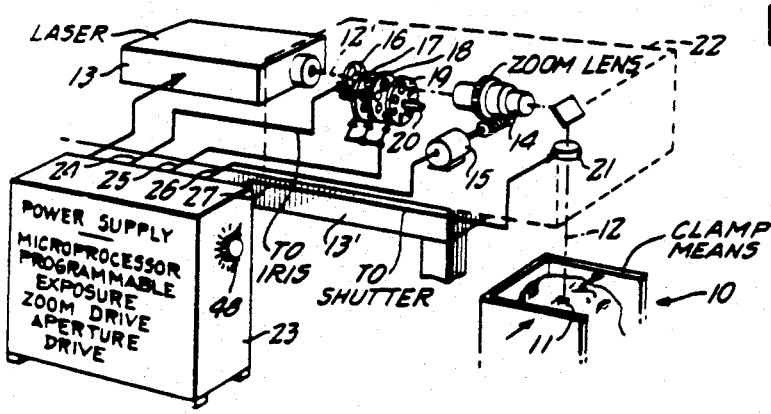
FIG. 1 is a schematic diagram in perspective, to show the general arrangement of operative components of the invention.

In FIG. 1, clamp means 10 is shown for fixed retention of the head of a patient (reclined, face up) such that the eye 11 to be operated upon is fixedly aligned with a downwardly folded portion 12 of the central axis 12' of beam output from a stationary laser device 13, supported by a table or other base 13'. The optical system of laser-beam projection to eye 11 includes zoom-lens means 14 having a reversible motor drive 15 whereby laser-spot size at eye 11 can be caused to vary. The optical system is further shown in FIG. 1 to include a variable-aperture iris 16, three aperture-mask discs 17, 18, 19 each of which is selectively indexible about an axis 20 offset from and parallel to beam 12', and a selectively operable shutter 21. The described optical-system components are preferably contained within a housing 22, which is only suggested by dashed lines, which will be understood as having entrance-port and exit-port windows as necessary to permit laser-beam delivery on alignment 12 to eye 11.

A cabinet 23 is shown by legend to include a power supply for the laser, and cabinet 23 is also shown by legend to include programmable microprocessor means for controlling exposure and beam (spot) size on axis 12 at impingement with the anterior surface of the cornea of eye 11, as will later become clear. Specific connections shown from cabinet 23 include line 24 for control of iris 16, a multiple-line cable 25 for selective indexing control of each of the discs 17, 18, 19, line 26 for reversible-drive control of zoom-lens magnification via motor 15, and line 27 for open/shut operation of shutter 21.

As in said L'Esperance, Jr. patents, clamp means 10 preferably includes means to stabilize the patient's head; this is schematically suggested by legend to be via opposed engagements at the region of his temples. An eye-retaining fixture such as shown and described in said patents may be used to peripherally engage eye 11 at the corneal-scleral area.

The laser selected for use at 13 emits at a tissue-ablating wavelength, which may be in the narrow water-absorption infrared band at or near 2.9 microns, but which is preferably in the far-ultraviolet region, as provided by an argon-fluoride laser at 193 nonometers. Various gas lasers operate at tissue-ablating ultraviolet wavelengths, and frequency-multiplying techniques applied to other lasers, including crystal lasers, provide further alternative sources.

One of the existing commercial excimer-laser products of Lambda Physik GmbH, Göttingen, Federal Republic of Germany, for example, their Model EMG 103 operating with argon-fluoride, is satisfactory for use as laser 13. Also satisfactory is one of the Series-2000 excimer-laser products of Questek, Inc., Billerica, Mass., operating with argon fluoride. It will be understood that the output beam of such lasers is rectangular and that such an output beam may be implemented by beam-expansion and homogenizing techniques, such that, for present purposes, the flux-density of laser-beam output will have been uniformly distributed across a square or circular beam section, prior to delivery on axis 12' to the spot-size control means within housing 22. It will also be understood that optical elements of lens 14 and other components transparent to involved laser radiation are of suitable materials, such as fused silica, calcium fluoride, and magnesium fluoride. Techniques of beam shaping and homogenization need not now be described, but the disclosure of Telfair, et al. application, Ser. No. 009,724, filed Feb. 2, 1987 (now superseded by continuation application Ser. No. 284,234, filed Dec. 14, 1988) is incorporated by reference, for such purpose.

Figure 2A:
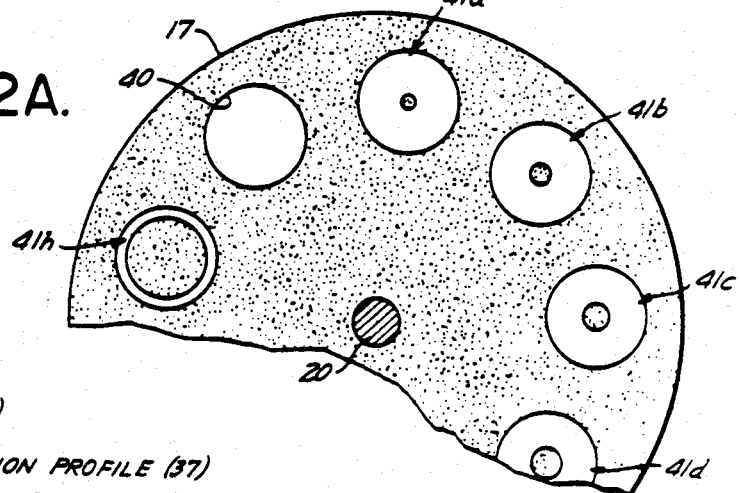
FIG. 2A is a fragmentary plan view of an indexible aperture mask of the invention, said mask being a component of FIG. 1.
Figure 2:
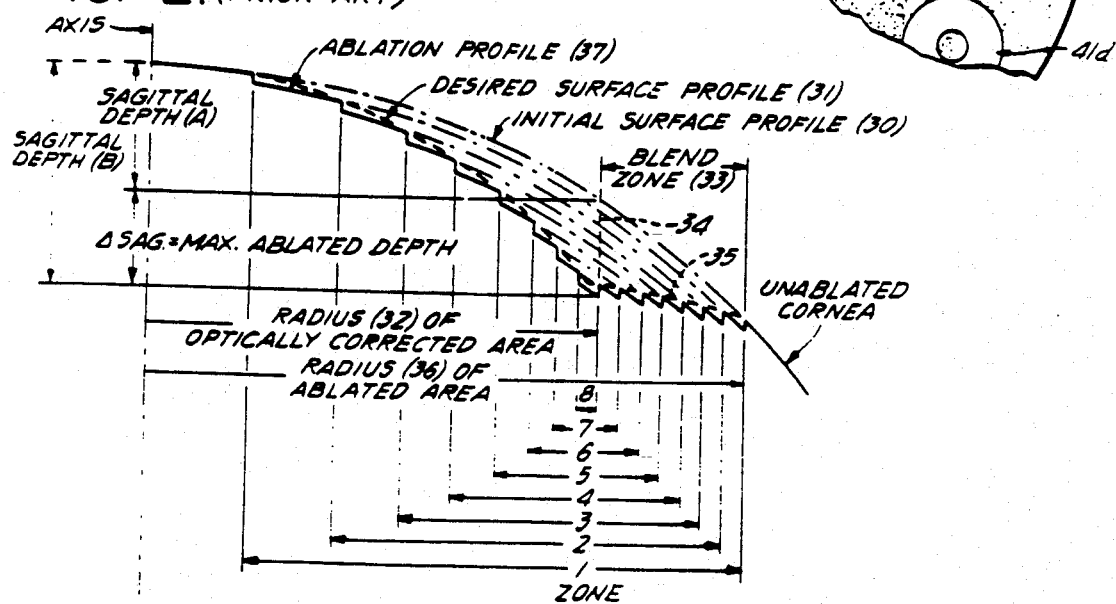
FIG. 2 is an enlarged half-section profile of the anterior surface of an eye having a hyperopia problem, together with an indication of progressively stepped ablation to achieve hyperopia reduction via an indexed-aperture mask of said L'Esperance, Jr. patents.

FIG. 2 has been labeled "Prior Art" because it is virtually entirely devoted to showing the hyperopia-correcting operation of an indexible aperture-disc embodiment of said L'Esperance, Jr. patents, and because this capability of said patents is the context from which to explain the present invention. In the FIG. 2 situation, the hyperopic eye has an initial anterior-surface profile 30 of too-great radius of spherical curvature, and it is desired to reduce the radius of spherical curvature into substantial conformance with a desired-surface profile, shown by dashed line 31, to the limiting extent of prescribed radius 32 of the optically used area of the cornea. As can be seen from legends in FIG. 2, such a desired optical correction proceeds from an initial sagittal depth A to a maximum sagittal depth B, involving an increase ($\Delta$ SAG.) of maximum ablated depth at the outer radius 32 of the optically corrected area; and were it not for providing a blend zone 33 of ablation radially outside and contiguous to the optically corrected area, a sharp annular wall 34 would be left to delay or frustrate post-surgical regrowth of epithelium over the ablated area. The desired blend-zone profile is indicated by dashed line 35, providing a gently sloped profile of transition out to the outer unablated region of the cornea.

In the example of FIG. 2, the indexible aperture disc provides eight annular apertures, and the exposure time (number of excimer-laser pulses) of laser radiation delivered to the cornea is the same for exposure through each of the successive annular apertures. The inner and outer radii, i.e., the annular zone, for each of these annular apertures, are shown by legend; and as explained in said L'Esperance, Jr. patents, each annular aperture is an opaque central spot, concentric within an outer circular limit of transparency of a suitable substrate which has been coated for opacity outside said limit. Experience has confirmed that, for argon-fluoride excimer lasers, as specified above, and as delivered, at appropriate and essentially constant energy density, through beam-homogenizing and shaping optical elements of the system described in said Telfair, et al. application, each excimer-laser pulse will ablate approximately 0.1-micron of incremental depth penetration into corneal tissue; thus, 100 such pulses at a given indexed aperture position will ablate an annulus of approximately 0.01-mm penetration depth. FIG. 5 tabulates descriptive data on aperture size and ablation diameters for the eight-zone indexible-disc situation depicted in FIG. 2, wherein there is only one optical system, of magnification 0.2800, interposed between the indexible disc and the cornea, and individual steps of the resulting ablation profile 37 are of 0.0102-mm height. It is to be cautioned that the tabulated figures assume uniform ablation depth of all steps of FIG. 2. However, theory and experience indicate that ablation depth effectively reduces in accordance with a cosine function of angle of laser-beam incidence on the cornea, reducing roughly 10 percent at radius 32, as compared with full-step height for the inner radius of zone 1. This effect can be compensated by appropriate small increases in number of pulses for the larger outside diameter apertures.

In accordance with the invention, step height (which is a function of (1) the number of successive mask apertures of the prior art, (2) the number of laser pulses per mask opening, and (3) the energy density of the laser beam at the cornea) is reducible to the extent of at least an order of magnitude when an apertured mask is used in conjunction with a zoom lens, as at 14, the latter being used solely as a means of effectively finely subdividing the steps of progression of beam-spot size at the cornea, between successive apertures of a given aperture disc 17, 18 or 19, each of which is of specialized configuration to serve the respective purposes of hyperopia reduction, myopia reduction, and astigmatism reduction. Since only one of the discs 17, 18, 19 is to be used for a given operation, each of these discs has one large and fully open indexible-aperture location, as at 40 in the case of hyperopia-reducing disc 17 of FIG. 2A, which location is indexible into concentric relation with beam axis 12' to permit use of a selected one of the two other discs 18, 19.

Also, in accordance with a feature of the invention and here specifically illustrated for the case of blend-zone (33) formation along with a hyperopia-reducing ablation procedure, an iris, as at 16, is variably controlled to define the progression of outer-diameter limitation delineated for the respective zones of the successive indexible apertures. This iris function at 16 will be understood to be smoothly continuously variable or in stepped progression, under microprocessor control and in synchronism with coordinating microprocessor control of disc (17) indexing and of zoom-lens setting, the latter being continuously variable or in stepped progression within a relatively narrow range of magnification change between any two adjacent indexible apertures of disc 17.

The programmed use of iris 16 to determine the succession of outer-diameter limits of annular-spot impingement at the eye necessarily means that the outer-diameter limits of the succession of annular apertures 41a, 41b, 41c . . . 44h are not controlling of delivered spot size; they are therefore seen in FIG. 2A to have the same maximum outer diameter which may be equal to the outer diameter of the fully open aperture 40. This condition is further supported by the illustrative tabulation of FIG. 5A, wherein iris-diameter settings and zoom-lens magnification settings are set forth in the context of constant maximum outer-diameter dimensioning of all eight zone apertures of disc 17.

It has been observed that both iris 16 and zoom-lens 14 are capable of continuous variation, and it will be understood that microprocessor means at 23 may be programmed to achieve such continuous variations, in suitably correlated synchronism with each other, for each of the zone-identifying indexible apertures of disc 17. However, the principle of step-size reduction through coordinated use of iris 16 and zoom lens 14 is adequately illustrated by FIG. 5A, for purposes of comparison with the prior-art techniques of FIG. 5, by using only three zoom and iris settings for each of the eight zone-indexed positions in a full 8-zone succession of using disc 17 (FIG. 2A). Thus, in FIG. 5, the first iris setting and the first zoom-lens setting, for each newly indexed zone-identifying aperture of disc 17, will be seen to be respectively equal to the corresponding outer disc-aperture diameter of FIG. 5 and to the constant magnification (0.2800) of FIG. 5. And between adjacent indexed-aperture openings, two stages of small incremental iris-opening changes and relatively small incremental magnification changes account for a trebling of the number of different spot sizes with which to accomplish the hyperopia-reducing ablation process. With a trebling of the number of different spot sizes, one accomplishes step-size reduction by a factor of three. And it should be clear without further explanation that to provide, say ten steps of iris setting and of coordinated zoom-lens setting for each indexed-aperture position of disc, will provide a 10-fold increase in the number of discrete steps per procedure, as well as a10-fold reduction in the size of individual steps, thus reducing to negligible proportions any deviation in ultimate desired profile with respect to the dashed-line profiles 31, 35 of FIG. 2.

Figure 3:
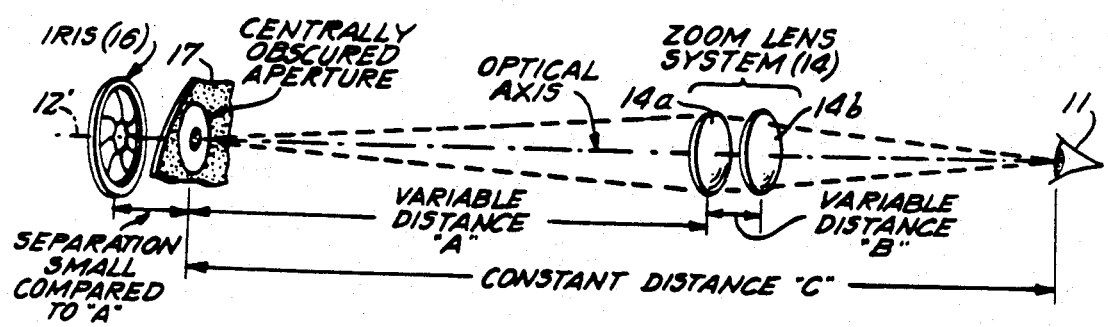
FIG. 3 is a simplified optical diagram to permit initial discussion of principles of the invention.

FIG. 3 serves to indicate basic relationships between optical components which determine spot-size control in the hyperopia-correction situation wherein one of the apertures 41a . . . 41h of disc 17 has been indexed into concentric relation with the central axis 12' of laser-beam projection. The zoom-lens system 14 operates over the constant object/image distance C and is seen to comprise two optical elements (or groups of optical elements) 14a, 14b which image, at eye 11, the central opaque area of the currently operative indexed annular aperture of disc 17; the imaging process involves an image reversal, which is of no adverse consequence for present purposes. Changes in image magnification result from motor (15) driven variation of the separating distance B between elements 14a, 14b as well as synchronized variation of the separating distance A between the aperture 17 and the lens 14a. And since iris setting is determinative of the currently effective outer diameter of the currently indexed aperture of disc 17, it is indicated by legend that axial separation between iris 16 and disc 17 is small compared to the variable object distance A, thus dictating a preference that the hyperopia-reduction disc 17 be adjacent to iris 16, and that remaining discs 18, 19 be at similarly small axial spacing from each other and from disc 17.

Figure 4:
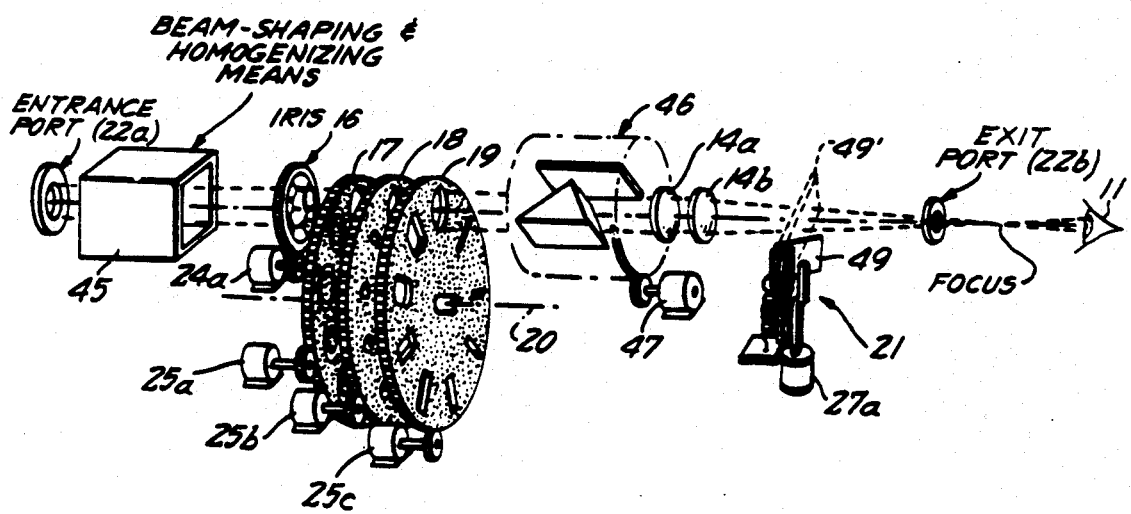
FIG. 4 is a more specific optical diagram in support of further discussion of principles.

FIG. 4 provides further detail of the means for spot-size control, between the laser-beam entrance port 22a of housing 22 and the exit port 22b of beam projection to eye 11, it being understood that the beam-folding mirror of FIG. 1 has been omitted for simplifying purposes. Thus, within housing 22, beam-shaping and homogenizing means 45 will be understood preferably to deliver to iris 16 a virtually collimated laser beam of circular section which is characterized by substantially homogeneous distribution of flux density, the circular section being large enough to circumferentially continuously lap iris 16 for its largest diameter opening, so that this largest iris opening can thereafter be determinative of the maximum outer diameter of aperture opening in any and all of discs 17, 18, 19. Iris (16) setting is shown to be variably operated by a reversible drive motor 25a which will be understood to be served by line 24 of FIG. 1. Each of the three indexible aperture discs 17, 18, 19 is shown to be independently positionable by its own indexing-drive motor 25a, 25b, 25c, respectively served by a different control-circuit line in cable 25 of FIG. 1. An image-rotating optical system 46 is bodily rotatable, as via edge-driven coupling to a drive motor 47 which will be understood to be controllable by knob setting 48 (at 23 in FIG. 1) for an astigmatism-correcting procedure to be described. The zoom-lens elements 14a, 14b and their relationships A, B, C have already been described in connection with FIG. 3. And, finally, shutter 21 is seen to comprise a pivoted opaque blade 49 which is spring-urged to closed position (49'), and which is actuated by solenoid means 27a to open position, under microprocessor control via line 27 of FIG. 1.

Figure 6:
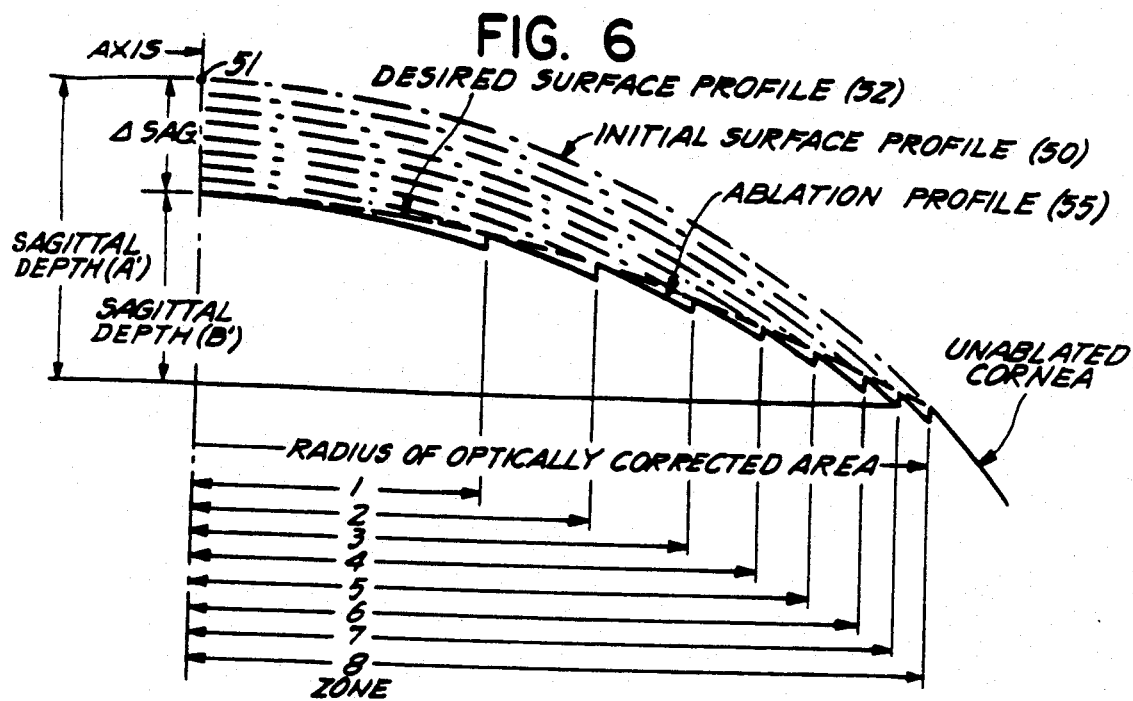
FIG. 6 is a view similar to FIG. 2, to permit discussion of use of the invention to reduce a myopia condition.
Figure 6A:
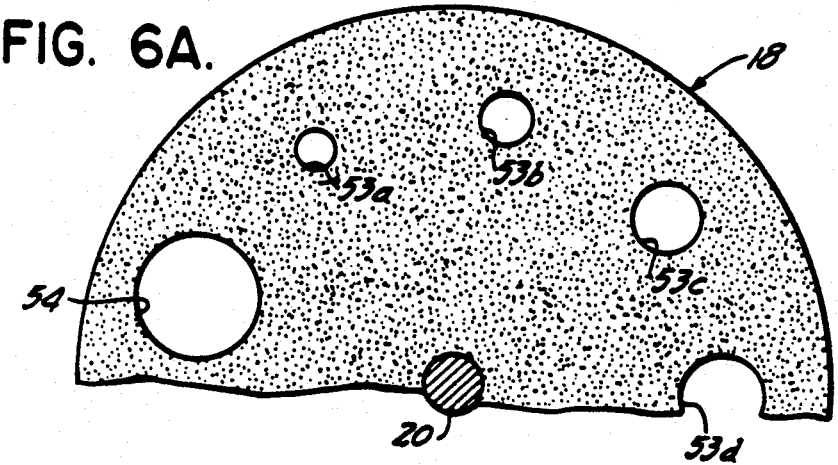
FIG. 6A is a fragmentary view similar to FIG. 2A, showing an indexible-aperture mask for reducing the myopia condition of FIG. 6.

FIGS. 6 and 6A illustrate myopia-reducing use of the invention with simplified drawings that are analogous to FIGS. 2 and 2A. The myopia-inducing initial anterior-surface profile 50 is, at intercept 51 with the optical axis of the eye, taken as the reference point for defining the sagittal depth A' of the optically used area of the eye (per profile 50) which is to be correctively ablated to a desired new profile 52 of greater spherical radius of curvature, with reduced sagittal depth B'. And maximum ablation depth ($\Delta$ SAG.) is at the central region of the eye. The first eight of nine apertures 53a, 53b, etc. of indexible disc 18 are circular and of progressively increasing diameter, consistent with the progression of zone radii shown in FIG. 6; the ninth aperture 54 is at least as large as the corresponding large opening 40 in disc 17, thus permitting myopia-correcting functions to be suppressed while one of the other discs 17, 19 is determinative of the selected sculpturing procedure. Without the coordinated zoom-lens functioning described for use in connection with FIG. 2A, the successively indexed myopia-reducing operation of disc 18 will sculpt a succession of eight stepped increments of tissue ablation, which could result in steps as large as 0.01-mm high in the resulting ablation profile 55, for the illustrative exposure time (number of pulses) assumed in the discussion of hyperopia correction. But with zoom-lens setting so controlled by the microprocessor as to substantially enlarge (e.g., by a factor of ten) the number of progressively changed step areas for each indexed one of the openings 53a, 53b, etc., the step-height increments become literally insignificant, and the desired-surface profile 52 is closely approached if not effectively realized.

Figure 7:
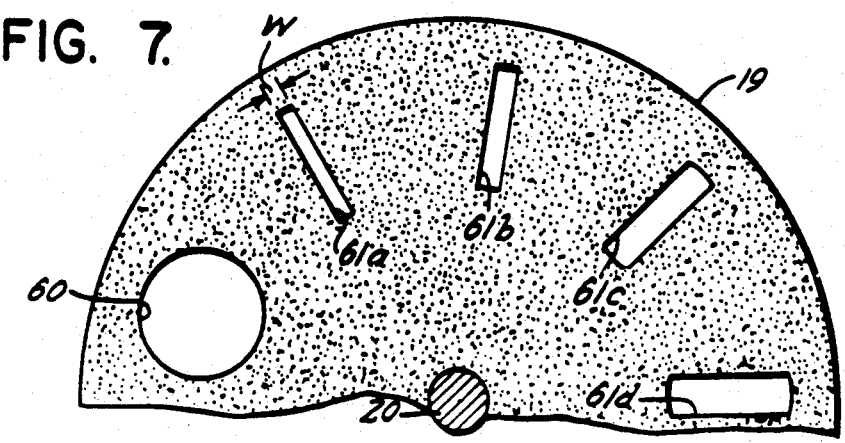
FIG. 7 is another frequency view of an indexible-aperture mask, similar to FIGS. 2A and 6A, but specifically applicable to ablation to reduce an astigmatism condition.

FIG. 7 is a view similar to FIG. 6A to illustrate a third indexible aperture disc 19, which is dedicated to reduction of astigmatism. As with the other discs, there are plural equally spaced apertures, one of which is a large-area circular opening 60, to permit operative use of one of the other two indexible-aperture discs 17, 18. For astigmatism reduction, each of the succession of openings 61a, 61b, 61c, etc. is a radially extending slit which is indexible into operative position, centered on the axis 12'; slit openings 61a, 61b, etc. are of length which may correspond with the diameter of large opening 60, and of lateral width W which progressively increases, for each successively indexed position of disc 19. Thus, if the sagittal depth of astigmatism-reducing ablation ($\Delta$ SAG.) is to be equivalent to that shown in FIG. 6 for myopia-reducing ablation, FIG. 6 may be taken as a half-section profile of the cylindrical curvature to be reduced for astigmatism correction. The cumulative effect of a full cycle of indexed disc-19 use will again be a stepped cylindrical ablation profile (as at 55), with eight relatively high steps, and at a certain angular orientation when imaged at the eye. The angle of orienting the beam rotator 46 of FIG. 4 will determine ultimate orientation of cylindrical ablation at the eye, and a prescription orientation of cylindrical-axis orientation may be selected by adjustment of knob 48 at control console 23 of FIG. 1. Again, it will be appreciated that by suitably programmed zoom-lens magnification control for each of the eight indexible slit openings of disc 19, a very much improved resultant profile of reduced cylindrical curvature is achieved, illustratively with an order of magnitude of improved approach to the desired profile.

In all of the foregoing discussion of iris, zoom-lens., and indexible-disc control to achieve a selected one of the three illustrative curvature changes, it has been assumed, for simplification purposes, that equal steps (i.e., ablated penetration depth increments) are to be achieved for each of the respective indexed positions of the selected indexible disc. As seen in FIGS. 2 and 6, this means that radial increments for each of the steps near the optical axis of the eye are larger than for each of the steps near the outer radius of the optically corrected area. Clearly, these radial increments are subject to choice, to the extent that, if desired, they may all be equal, or they may be smaller near the optical axis and larger near the outer radius of the optically corrected area, and the magnification control of zoom-lens setting may be selected as appropriate to achieve virtually any fineness of subdividing step allocation for each of the indexed-aperture positions of the involved one of discs 17, 18, 19.

A typical cycle of laser-beam exposure to achieve a given curvature correction, all under microprocessor control, can be as follows:

(1) With shutter closed, with a particular disc 17, 18, or 19 selected for its particular sculpturing function, and with the number of exposure pulses selected to achieve the maximum tissue-ablating depth for the prescribed diopter change at a given maximum radius of optically corrected area, initiate laser operation and check its output for specified amplitude and homogeneity of flux distribution. As a result of such selection, the two remaining discs (which are not to be used) will have been automatically indexed to place their large-opening positions concentric with the beam axis 12', and the selected disc will have been indexed to place the initial one of its eight progressively varying apertures on the beam axis.

(2) Operation is initiated by opening shutter 21, for a period of time (number of pulses) which reflects measured exposure through the first of the eight progressive apertures, while zoom-lens settings (and, if disc 17 is used, also iris-aperture settings) are modified pursuant to microprocessor control. At microprocessor-determined conclusion of exposure for the first indexible aperture position, shutter 21 is closed, and under microprocessor control, the selected disc is advanced to the next indexed aperture, while zoom-lens setting (and, if applicable, iris-aperture setting) is re-established as needed for use at the second index position of the selected disc, whereupon shutter 21 is automatically opened to permit exposure for the second phase of controlled variation of zoom magnification (and, if applicable, iris-aperture variation).

(3) Cycles as in (2) above are program-controlled to repeat, as appropriate for each of the eight indexible positions of the selected disc, each being accompanied by controlled variation zoom-magnification (and, if applicable, iris-aperture variation).

(4) Laser 13 is automatically shut down at shutter 21 closure, upon completion of the requisite number of cycles, being eight for the illustrative case of eight indexible-mask apertures for each disc.

As explained above, the zoom-lens/indexed-aperture example of FIG. 5A represents simplification, in that the same exposure time (number of pulses) is used for each indexed setting of the indexible-mask wheel (17, 18 or 19). This necessarily means that for each indexed-aperture position, the zoom-lens magnification proceeds through the greatest range of variation for aperture 41a, as compared with subsequently indexed apertures.

As another means of distributing laser-beam exposure to the cornea for a given procedure of optical curvature change, e.g., for more equal increments of radius of ablation throughout the entire optically corrected area to be ablated, it is possible to so select the number of mask apertures and the increments of mask-aperture dimensions that, in conjunction with continuously varying zoom operation and with different numbers of pulses allocated to each indexed aperture, more nearly uniform increments of ablated radius are achieved throughout the full course of the procedure. For example, in a myopia-correcting situation, four different indexed apertures (53a, 53b, 53c, 53d) can suffice if selected at four successive radius-doubling increments of radius. Specifically, four such apertures, illustrative at 1.562-mm, 3.125-mm, 6.250-mm, and 12.500-mm diameter, can be indexed-programmed for pulsed utilization with zoom lens 14 to require no more than a 1:2 zoom-lens range of continuous magnification change, for expanding-magnification action at each indexed aperture, so as to achieve a combined range of zoom-lens and indexed-disc coaction, from 1.562-mm diameter to 25.000-mm diameter, corresponding to 0.437-mm to 5.000-mm ablation diameter, where the 1:2 range involves limiting magnifications of 0.200 and 0.400, respectively. For this range, and for an approximately 3-diopter reduction in myopia, laser-pulse allocation may illustratively be:

20 pulses for the 1.562-mm aperture with zoom control of the ablation range 0.312-mm to 0.625-mm diameter.

40 pulses for the 3.125-mm aperture, with zoom control of the ablation range 0.625-mm to 1.250-mm diameter.

80 pulses for the 6.250-mm aperture, with zoom control of the ablation range 1.250-mm to 2.500-mm diameter.

160 pulses for the 12.500-mm aperture, with zoom control of the ablation range 2.500-mm diameter to 5.000-mm diameter.

It will be seen that in this illustrative case, the order of magnitude of incremental radial expansion, per pulse, for a 300-pulse treatment, is 0.015-mm per laser pulse.

It is to be understood that all examples given in the foregoing discussion are for illustrative purposes only, to show inter alia that the equal-step concept of the prior art, as per profile 37 of FIG. 2 or as per profile 55 of FIG. 6 is not to be considered mandatory or even preferred, in the programmed coordination of zoom-lens control, with indexing control and with indexed-aperture size selection. The selection of coordinated control has been shown to be also achievable on the basis of substantially uniform incrementing of ablating radius throughout a given surgical procedure, without imposing more than a 1:2 magnification-range capability on the zoom lens. Other types of programs are also devisable, the important point being that an almost perfectly smooth new curvature profile is made possible in spite of changing flux density, by relying upon a predetermined program of indexing the mask apertures of a given disc (17, 18 or 19) in coordination with laser-exposure time (i.e., number of pulses) at each indexed position and in coordination with the particular zoom-magnification range desired for each indexed-aperture position. It will be further understood, that, depending upon the program selected for a given hyperopia-reducing procedure, the aperture control of iris 16 must also be coordinated with zoom-lens magnification, to achieve the smooth blend profile 35, for the larger radius outside the radius 32 of the optically corrected area.

Also, by way of example, with magnification ratios always within the range 1:1.414, and providing stepped aperture increments of radius accordingly, the range of density variation with a given zoom use of any single aperture is maintained within the range 1:2.

The foregoing discussion involves different examples of sculpturing procedures which employ indexed apertures in conjunction with controlled variation of zoom-lens magnification, and is also illustrative of how parameters of a given program can be selected to minimize the range within which magnification varies, in the course of a given procedure. This is an important factor in the controlled ablation of corneal tissue, using the irradiating output of an excimer laser of the character indicated above, wherein laser-beam flux density should be held within relatively narrow limits, such as a dynamic range of 4:1 if ablation is to be reliably achieved. Preferably, the flux density of the beam at impact with corneal tissue should be as near constant as is possible.

Figure 1A:
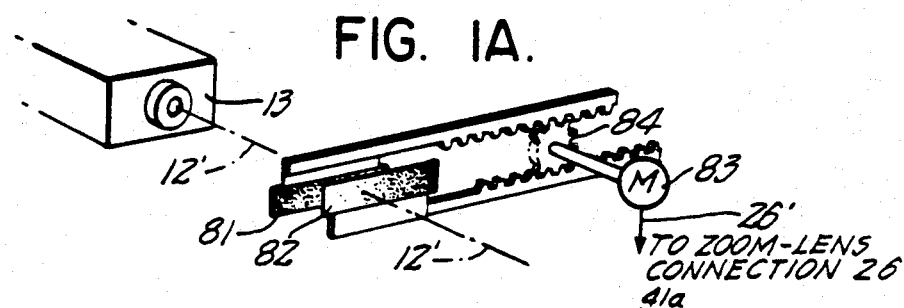
FIG. 1A is a fragmentary detail of a modified arrangement for a part of FIG. 1.

To achieve substantially constant flux density at the cornea, in the circumstance of varying magnification, a synchronizing provision can be built into the microprocessor program whereby laser 13 is controlled for increasing output intensity as a synchronized function of increasing zoom-lens magnification, using control connections schematically shown in FIG. 1, between the power-supply/microprocessor unit 23 and the respective laser (13) and zoom-lens adjustment (15) means. Alternatively, a single optical filter with rotational or uniaxial spatially variable optical density could be interposed between the point of laser (13) output and the spot-size determining elements (16, 17, 18, 19), or in any event positioned upstream from the zoom lens 14, and such optical filter can be displaceably driven to variably attenuate the laser beam in inverse relation to the instantaneous magnification of the zoom lens 14. However, in the fragmentary diagram of FIG. 1A, I show a present preference for an arrangement of two such filters 81, 82 acting in opposition upon axis 12' and driven by a motor 83 having suitably synchronizing connection 26' to the connection 26 for zoom-lens control. Specifically, shading for filter 81 is indicative of reducing density from left to right, and shading for an identical filter 82 is indicative of increasing density from left to right; and a reversible motor 83 for differential rectilinear rack drives, via pinion (84) engagement to both racks, assures balance in attenuation across the beam aperture of laser 13.

With the synchronized attenuation function achievable via the adjustment at 81, 82, 83, the laser 13 need only be set for a slightly greater output intensity than needed for ablation purposes, because attenuation functions of filters 81, 82 and of zoom-lens magnification will be in such synchronized inverse relation as to assure desired substantially constant delivery of tissue-ablating flux-density to the cornea at all operational phases of a given procedure.

FIGS. 8, 8A and 8B are similar half-section profile diagrams as in FIG. 2 but in illustration of utility of the invention for purposes of preparing a cornea for reception of a corneal transplant, in the circumstance wherein the laser beam is not characterized by sufficiently homogeneous flux (intensity) distribution. The above-identified L'Esperance, Jr. patents describe preparation for a corneal transplant, i.e., a straight constant-diameter ablative removal of corneal tissue to a uniform depth, wherein original anterior surface curvature is replicated at the floor of the constant-diameter incision, but the assumption is made in said patents that the laser-beam section is characterized by a homogeneous distribution of flux density. Subsequent experience is that a homogeneous distribution of flux density is not readily achievable with currently available excimer lasers, which characteristically have a more or less Gaussian profile in one meridian, and a nearly "top-hat" profile in the orthogonal meridian; and even if optical or beam-rotating means are employed in an effort to make the flux-density profile more nearly uniform, the result is generally an axisymmetric profile, with approximately parabolic fall-off, from axis to edge. Other laser types may deliver a beam with a Gaussian fall-off, from axis to edge, but for simplified present discussion, the expression "parabolic" is adopted in reference to an ablating-laser beam section, with fall-off from axis to edge.

FIG. 8 illustrates that, despite intensity fall-off in the laser beam, the presently described apparatus can be used to prepare a cornea to a uniform depth Z for reception of a corneal transplant of given radius 70. To this end, the microprocessor will have been programmed to select one of the apertures of masking disc 18, in conjunction with suitable adjustment of zoom lens 14, whereby the beam section impacting the cornea is of the given radius 70. But since the beam section has (or with beam rotation delivers) a fall-off intensity distribution that is somewhat parabolic, the initial anterior-surface profile 71 cannot be replicated (at 71') at the desired depth Z; on the other hand, exposure to the parabolic intensity distribution results in an ablated floor profile 72 which is of different curvature, ranging from the full desired depth Z on the axis of beam delivery, but falling off to a laser depth $Z_1$ at the radius 70 of the preparation; the extent of the short fall at radius 70 is designated $\Delta Z$ in FIG. 8.

FIG. 8A illustrates that, with microprocessor control of laser-beam exposure through successive apertures of a hyperopia-correcting mask (such as the mask 17), and with radius 70 maintained as described above (e.g., by one of the apertures of disc 18, in conjunction with the indicated adjustment of zoom lens 14), it is possible to continue the program described in connection with FIG. 8, using what would otherwise be a hyperopia-correcting program. The result of such a program is an incrementally stepped ablated-surface floor, shown with exaggeration by solid line 73; these steps will be understood to correspond with successive annuli ($74d$ through $74h$) of laser-beam exposure through mask apertures such as the apertures $41d$ through $41h$ of mask 17.

FIG. 8B illustrates further that, again with suitable microprocessor control, involving coordinated use of mask-indexing and zoom-lens variation, a much more smoothly developed floor profile 75 can be achieved, without involving zoom-lens magnification beyond a predetermined range limit. In such an application, a fixed outer limit of exposed area must account for the desired constant radius 70 of the ablation process, and this fixed outer limit must be determined by means (e.g., at shutter 21) between the zoom lens 14 and the patient's cornea; this is a simple matter of assuring that when shutter 21 (FIG. 1) is open, it presents a circular aperture which determines the constant radius 70 at beam impingement upon the cornea.

If it is determined that the range of zoom-lens magnification is 1:2, then an indexible mask of the nature shown in FIG. 2A need only have four apertures; but if the range of zoom-lens magnification is to be 1:1.414, then there should be twice as many apertures. In FIG. 8B, the symbolism $R_1, R_2 \ldots R_8$ will be understood to identify successive outer radii attributable to the central opaque spot in each of a succession of eight apertures in an indexible mask 17; and the additional parenthetical and primed entry adjacent each such radius is to be understood as designating the radius to which the coordinated zoom-lens adjustment can account for radius expansion for exposure via a particular indexed aperture. Thus, for example, for the mask aperture having the smallest-diameter central spot, the designation $R_1$ ($R_2'$) is to be understood as indicating the range of radius expansion (i.e., $R_1$ to $R_2$) available for this smallest central spot, within the indicated 1:1.414 magnification range of a coordinated control of zoom-lens setting. Similar designations $R_2$ ($R_3'$), $R_3$ ($R_4'$), $R_4$ ($R_5'$) ... $R_8$ ($R_9'$) apply for the respective indexed apertures of the mask, as the central spot is indexed to grow, for each successive aperture use of the same controlled 1:1.414 magnification range of zoom lens 14. And it is to be understood that coordinated equalizing adjustment is preferred for beam intensity control as a function of zoom-lens magnification, as explained above in connection with FIG. 1A. The result is the smoothed profile 75, representing essentially constant depth of ablating penetration of the cornea, to depth Z.

FIG. 9 illustrates much of what has been described in connection with FIGS. 8, 8A, 8B, except for the formation of a blend or bevel 76 beyond the optically used radius, to encourage epithelium regrowth over a newly sculpted surface 75' of constant depth Z with respect to the original contour 71' of the anterior surface of the cornea. But, in the case of FIG. 9, the original contour 71' of an otherwise perfect cornea, is marred by a scar or other wound 77 which has only partially invaded the cornea, and the object of the sculpturing procedure is to select a constant depth Z which is sufficient to eliminate the wound, so that the patient's cornea can be resurfaced to his own good curvature at 75', with relatively prompt epithelium regrowth over the refinished surface.

To prepare for the operation of FIG. 9, the volume of wound 77 should be filled with epithelium or other suitably viscous material (such as a drop of 1% methyl cellulose) having substantially the same ablation response to the laser beam as is the case for corneal tissue to be ablated to depth Z; wound filling should be made to essentially the original contour 71'

Presently described apparatus can perform the involved operation, in the indicated circumstances of a laser beam having a parabolic profile of fall-off distribution of flux density, under the following set-up conditions, for a two-step procedure:

STEP 1. The control of iris 16 is programmed to determine the outer-radius limit of beam exposure to the cornea in synchronized coordination with instantaneous zoom-lens setting, so as to determine the outer radius $(70+\Delta R)$ of blend 76 at the outset, and so as to gradually reduce this outer radius by the decrement $\Delta R'$, as of the time $T_1$ when steady exposure (determined by the thus-varying iris aperture) has achieved the depth Z of ablated penetration on the axis of beam delivery.

STEP 2. Having achieved STEP 1, shutter 21 is actuated to transiently cut off beam delivery while a suitable hyperopia-reducing masking disc 17 is indexed into its first operative position, e.g., with its central opaque spot, in coordination with zoom-lens control, determining varying radius in the range from $R_1$ to $R_2$ (as in FIG. 8B); for purposes of STEP 2, it will be understood that the annular apertures of disc 17 will have been selected such that the outer radius of the annular aperture is not a limitation on delivered outer radius $(70+\Delta R-\Delta R')$ of the laser beam, so that the STEP-1 program of iris coordination with zoom-lens control can continue the further development of the blend or bevel 76 throughout the full STEP-2 exposure, from time $T_1$ to time $T_2$. Shutter operation repeats for each indexing of successive apertures of the mask 17; and zoom-lens control in the range 1:1.414 together with beam-equalizing control, recycle as appropriate for exposures through each of the successively indeed apertures of mask 17. At time $T_2$, the operation is complete, and the desired contours 75' and 76 have been established. The patient need only await the approximately two-day period for epithelium regrowth, and he can then use his resurfaced cornea.

FIGS. 10 to 13 illustrate further uses and applications of above-discussed principles, and for the sake of simplicity, these particular drawings have been presented for an assumed beam-energy distribution that is uniform across the beam, in each case. Also for simplicity of presentation, these drawings illustratively plot ablation depth as a function of radius about the axis of the eye, as if the anterior surface of the cornea were a plane surface; thus, it will be understood that for the points to be made in connection with FIGS. 10 to 13, additional compensation will have to be made for the parabolic fall-off and for the cosine effect of such beam obliquities as are at radial offset from the eye axis.

Figure 10:
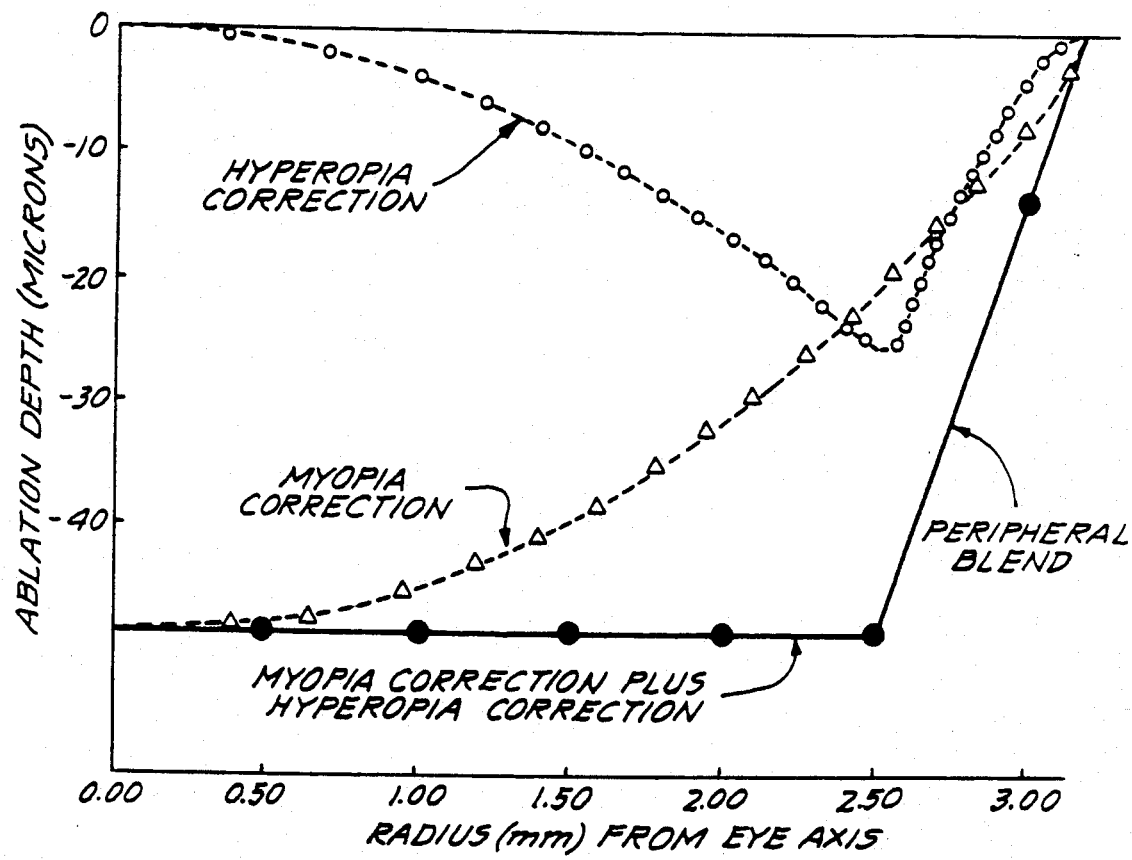
FIGS. 10 to 13 are similar diagrams to illustrate further techniques to eliminate scar or other wound damage to the cornea.

The case of FIG. 10 depicts the combined use of a myopia-correcting procedure and of a hyperopia-correction procedure, to achieve a uniform depth of penetration into the stroma, over the optically used area of the cornea. Labels separately identify the sculpturing profile achieved separately by a myopia-correcting program and by a hyperopia-correcting program. In the case of FIG. 10, the myopia-correcting program is selected to cover a circular area which is larger than that required for optical use, to the extent that the area of myopia-reducing procedure equals the area needed to accommodate the annular blend region of the hyperopia-reducing program. The net result of having programmed the myopia-reducing procedure to cover the full penetration depth needed to eliminate a scar or wound (as at 77 in FIG. 9), and of having programmed the hyperopia-reducing procedure to achieve a lesser maximum penetration depth than for the myopia-reducing program, can be to produce a composite ablation to the uniform depth shown, for the entire optically used area of the cornea; and at the same time, an annular peripheral blend zone is achieved outside the optically used area, it being noted that both procedures contribute to definition of the blend zone.

To compensate for the kind of parabolic fall-off discussed above, it is merely necessary to program the microprocessor for suitable adjustment of the number of pulses delivered at each aperture (discs 17, 18, and iris 16, as discussed above in connection with FIG. 4), or otherwise, in the event of zoom-coordinated operation. The same kind of compensation for the cosine effect attributable to obliquity of the beam at incidence with the curved surface of the cornea (typically, a radius of curvature of about 7.5-mm) can also be made by selection of number of pulses delivered as a function of spot size and shape in the course of each procedure.

Figure 11:
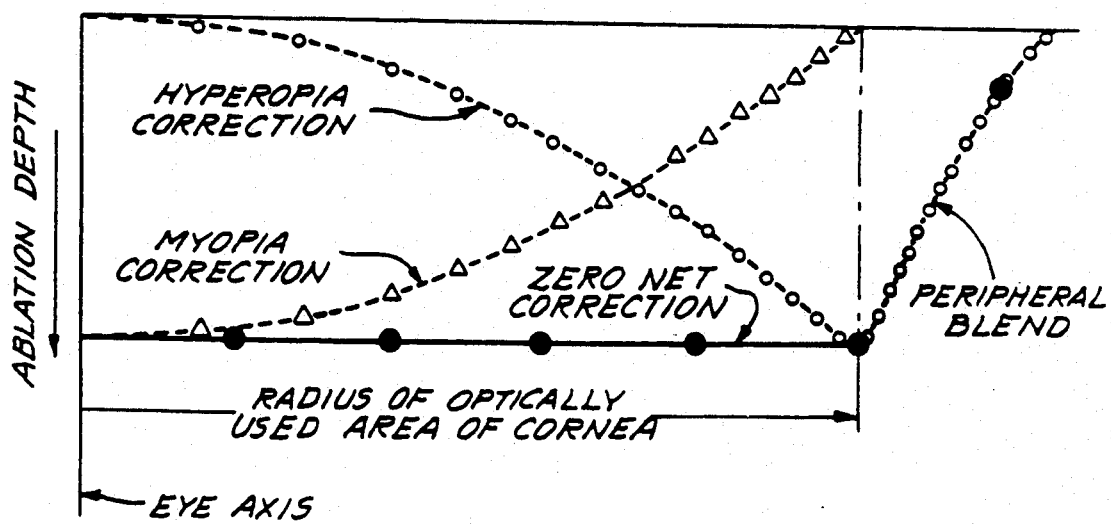

FIG. 11 illustrates a variation wherein the hyperopia-correcting and myopia-correcting curvature programs are selected for equal maximum-depth penetration and for equal areas of curvature correction which match the optically used area of the cornea. The hyperopia-correcting program was additionally selected for its additional definition of the peripheral blend zone. The apparatus to achieve this result can involve an indexible mask of the kind described for hyperopia-correction in said L'Esperance, Jr. U.S. Pat. Nos. 4,729,372 and 4,732,148.

It will be understood that the procedures discussed above in connection with FIGS. 10 and 11 are particularly applicable to a patient having good eyesight but who has accidentally been wounded in the cornea. The fact that the FIG. 10 and FIG. 11 procedures can accomplish uniform depth penetration means that the patient's good eyesight (i.e., his original corneal curvature) can be recreated without the scar or other wound.

Figure 12:
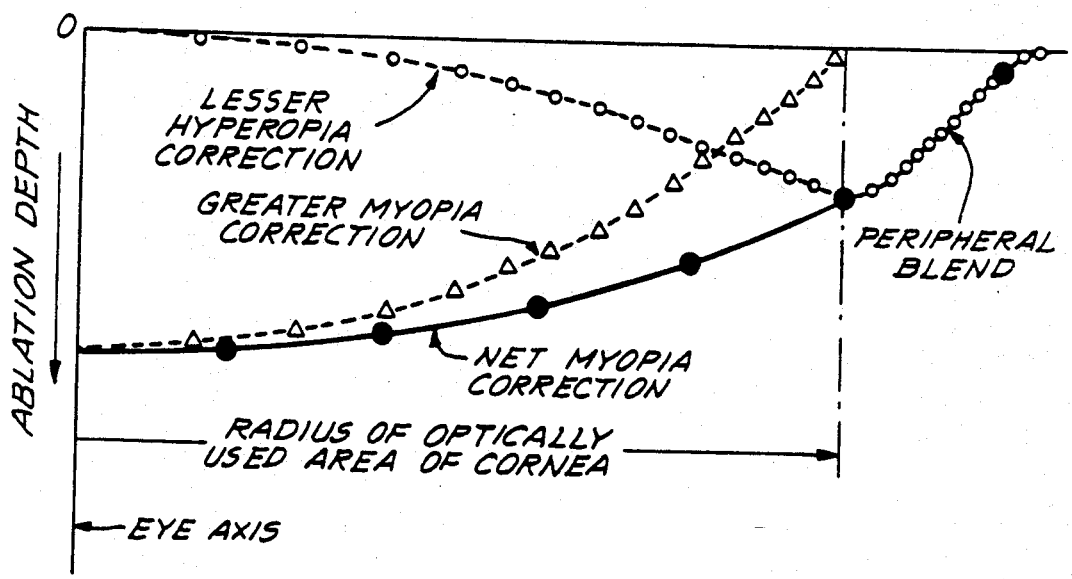
Figure 13:
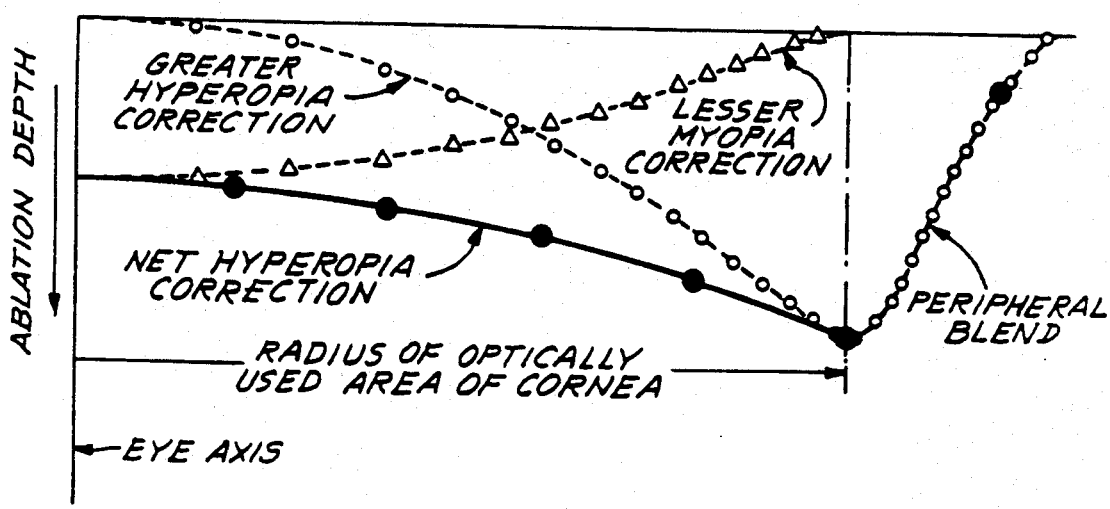

Another kind of accident can also affect a patient who has been relying upon spectacles or a contact lens to correct his defective vision. The accident may fracture a lens, and a lens fragment may cause the wound (as at 77, in FIG. 9). In this situation, the invention makes it possible to eliminate the wound and to give the patient a new corneal curvature which eliminates his need for a corrective lens. FIGS. 12 and 13 are on the style of FIG. 11, but are respectively illustrative of the use of the invention to achieve a net myopia correction (FIG. 12) or to achieve a net hyperopia correction (FIG. 13). In the case of FIG. 12, a greater penetration depth of the myopia-correcting program, as compared with that of the hyperopia-correcting program, is seen to result in a net myopia-correction profile which not only eliminates the wound but also provides a blend region outside the optically used area of the cornea. In the case of FIG. 13, a greater penetration depth of the hyperopia-correcting program, as compared with that of the myopia-correcting program, is seen to result in a net hyperopia-correction profile which not only eliminates the wound but also provides a blend region outside the optically used area of the cornea.

Although the above descriptions in connection with FIGS. 10 to 13 have assumed initial use of the myopia-reducing program, before use of the hyperopia-reducing program, it will be understood that this order of events is not mandatory, in that the same net result is achieved, whichever of the two procedures is first used in a given surgical operation. The described order, namely, myopia-reduction first, is preferred because this happens now to have seen first use on three patients, with successful outcome, in that examination after ablation revealed (1) approximately uniform depth penetration and (2) that the damaged tissue had been removed. These particular patients had no need for optical correction, but the principles of wound-removing operation are equally applicable to optical correction while also removing a wound. Also, it will be understood that, if, for example, the myopia-reducing program of FIG. 12 is viewed as in a section plane which is symmetrically oriented with respect to the patient's diagnosed astigmatism axis, then use of the disc 19 (FIGS. 4 and 7) in conjunction with orientation selection via rotator 46, will enable the corrective procedure to include an astimatism reduction while also removing the wound.

In all cases, whatever the procedure or combination of procedures selected for surgery on a particular patient, it is preferred as an initial step to remove epithelium from the area of the cornea to which the ablating exposure is to be made; such procedures are described in L'Esperance, Jr. U.S. Pat. Nos. 4,770,172, 4,773,414 and 4,798,204. In the case of a wounded cornea (as at 77 in FIG. 9), removed epithelium is a suitable filler for any void of the wound, and this should be applied to create a smooth surface for the ablative laser exposure. In all indicated operations, it is evident that the described apparatus is programmable for the indicated purposes, including compensating purposes, even in the presence of a parabolic or other characteristic fall-off of intensity distribution in the laser beam or in recognition of the cosine effect of obliquity of laser-beam impact with off-axis regions of the optically used area of the cornea.

What is claimed is:

1. Sculpture apparatus for making a uniform-depth constant-area ablated removal of corneal tissue in preparation for reception of a corneal transplant in an optically used area of the anterior surface of the cornea of an eye, said apparatus comprising laser means for producing a tissue-ablating output beam on a central axis of beam delivery to said area, the intensity distribution of laser-beam projection on said axis exhibiting substantially the same profile of fall-off in all radially outward directions from said axis, whereby for a given exposure of only said beam to said area, a curvature-decreasing change is effected at the anterior surface of the cornea, with depth of tissue-ablating penetration greatest at the center of said area and with penetration depth exhibiting substantially the same profile of fall-off in all radially outward directions from the center of said area, and controllable means for variably limiting the sectional area of said beam at impingement with the cornea, said controllable means including at least one indexible mask having a plurality of annular mask apertures of progressively changing inner radius, and control means connected to said laser means and to said controllable means for so controlling successive exposures via a succession of indexed mask apertures as to produce a curvature-increasing change, to the extent that a net substantially uniform depth of ablation of corneal tissue is achieved to said greatest depth over at least said optically used area.

2. Sculpture apparatus for making a uniform-depth constant-area ablated removal of corneal tissue in preparation for reception of a corneal transplant in an optically used area of the anterior surface of the cornea of an eye, said apparatus comprising laser means for producing a tissue-ablating output beam on a central axis of beam delivery to said area, the intensity distribution of laser-beam projection on said axis exhibiting substantially the same profile of fall-off in all radially outward directions from said axis, whereby for a given exposure of only said beam to said area, a curvature-decreasing change is effected at the anterior surface of the cornea, with depth of tissue-ablating penetration greatest at the center of said area and with penetration depth exhibiting substantially the same fall-off in all radially outward directions from the center of said area, and controllable means for variably limiting the sectional area of said beam at impingement with the cornea, said controllable means including (a) a zoom-lens system and (b) at least one indexible mask having a plurality of annular mask apertures of progressively changing inner radius, and control means connected to said laser means and to said controllable means for so controlling zoom-lens setting for each of a plurality of indexed apertures of said mask as to produce a curvature-increasing change, to the extent that a net uniform-depth ablation of corneal tissue is achieved to said greatest depth over at least said optically used area.

3. Sculpture apparatus for operation upon the anterior surface of the cornea of an eye, said apparatus comprising laser means for producing a tissue-ablating output beam and controllable means for variably limiting the sectional are of said beam at impingement on the cornea, the area variation being over a range which at least includes a maximum optically used area to be ablated and being symmetrical with respect to an axis of beam-projection to the cornea, and flux-density distribution across the beam-projection axis being at maximum near the beam-projection axis and diminishing with distance away from the beam-projection axis; said controllable means including;
(a) at least one indexible mask having a plurality of circular mask apertures of progressively changing radius;
(b) at least one indexible mask having a plurality of annular mask apertures of progressively changing inner radius; and (c) control means connected to said laser means and to said controllable means for so controlling the successive use of said masks as to produce a uniform-depth ablation of corneal tissue at least over said optically used area.

4. Sculpture apparatus according to claim 3, in which successive of the annular mask apertures are characterized by outer radii which progressively expand outwardly of the maximum radius of the circular-mask apertures.

5. Sculpture apparatus according to claim 3, wherein said controllable means further includes at least one indexible mask having a plurality of elongate rectangular apertures of progressively changing width, and selectively operable means for orienting the said rectangular apertures for successive rectangular-spot delivery wherein the elongation extends diametrically through the axis of beam projection to the cornea and at an angular orientation to effect an astigmatism correction.

6. Sculpture apparatus for operation upon the anterior surface of the cornea of an eye, said apparatus comprising laser means for producing a tissue-ablating output beam and controllable means for variably limiting the sectional area of said beam at impingement on the cornea, the area variation being over a range which at least includes a maximum optically used area to be ablated and being symmetrical with respect to an axis of beam-projection to the cornea, and flux-density distribution across the beam-projection axis being at maximum near the beam-projection axis and diminishing with distance away from the beam-projection axis; said controllable means including:
(a) at least one masking means for producing circular-spot delivery of progressively changing radius;
(b) at least one masking means for producing annular-spot delivery of progressively changing inner radius; and
(c) control means connected to said laser means and to said controllable means for so controlling the successive use of said respective masking means as to effect at least a predetermined depth of stroma-penetration over the entire optically used area of the cornea as well as a predetermined anterior-surface contour.

7. Sculpture apparatus according to claim 6, in which said masking means for producing annular-spot delivery is further characterized by production of outer radii which progressively expand outwardly of the maximum radius of circular-spot delivery.

8. Sculpture apparatus for curvature-correcting operation upon the anterior surface of an eye, said apparatus comprising laser means for producing a tissue-ablating output beam and controllable means for variably limiting the sectional area of said beam at impingement on the cornea, the area variation being over a range which at least includes a maximum curvature-correcting area to be ablated and being symmetrical with respect to a beam-projection axis which coincides with the optical axis of the eye, the intensity of laser-beam projection being limited per unit time to ablate but a fraction of a predetermined maximum depth of ablation into the stroma region of the cornea, said controllable means including (a) a zoom-lens system and (b) an indexible mask having a plurality of mask apertures of progressively changing area, and control means connected to said laser means and to said controllable means for so controlling zoom-lens setting for each of an indexed plurality of the apertures of said mask as to produce a relatively smooth variation of the sectional area of said beam at impingement of the cornea with an accompanying diopter change in the cornea, said relatively smooth variation being as compared with the stepped variation produced by use of the mask alone, the number of mask apertures and the relation of area change between one and the next mask aperture through the progression of area change being selected for limitation of requisite zoom-lens magnification to the range 1:1.414 or less, for each of the indexed positions of said mask, whereby the variation in energy density at the cornea is within the range 1:2.

9. Sculpture apparatus for curvature-correcting operation upon the anterior surface of the cornea of an eye, said apparatus comprising pulsing laser means for producing a succession of tissue-ablating pules in an output beam and controllable means for variably limiting the sectional area of said beam at impingement on the cornea, the area variation being over a range which at least includes a maximum curvature-correcting area to be ablated and being symmetrical with respect to a beam-projection axis which coincides with the optical axis of the eye, the intensity of laser-beam projection being such that corneal-tissue ablation per pulse is but a fraction of desired maximum ablation into the stroma region of the cornea, said controllable means including (a) a zoom-lens system and (b) an indexible mask having a plurality of mask apertures of progressively changing area, and control means connected to said laser means and to said controllable means for so variably controlling zoom-lens setting for each of an indexed plurality of apertures of said mask as to deliver a plurality of pulses in the course of zoom-lens variation for each of said indexed plurality of mask apertures whereby to achieve a relatively smooth variation of the sectional area of said beam at impingement on the cornea with an accompanying diopter change at the cornea, said relatively smooth variation being as compared with the stepped variation produced by use of the mask alone, the number of mask apertures and the relation of area change between one and the next mask aperture through the progression of area change being selected for limitation of requisite zoom-lens magnification to the range 1:1.414 or less, for each of the indexed positions of said mask, whereby the variation in energy density at the cornea is within the range 1:2.

10. Sculpture apparatus according to claim 8 or claim 9, in which the mask apertures are circular and or progressively changing radius, whereby to effect a relatively smoothly profiled myopia-correcting diopter change.

11. Sculpture apparatus according to claim 8 or claim 9, in which the mask apertures are elongate rectangular and of progressively changing lateral width, and selectively operable means for orienting the elongation axes of said apertures in accordance with a predetermined orientation of desired astigmatism correction, whereby to effect a relatively smoothly profiled cylindrical diopter change.

12. Sculpture apparatus according to claim 8 or claim 9, in which the mask apertures are circularly annular and of progressively changing inner radius, and in which said mask apertures are of outer radius which when projected to the cornea via said zoom-lens system is greater than that of the maximum curvature-correcting area to be ablated, said controllable means further including continuously variable-iris means for varying said outer radius, said control means so coordinating iris aperture with zoom-lens setting and with currently indexed mask aperture as to effect a relatively smoothly profiled hyperopia-correcting diopter change within said maximum curvature-correcting area and also to effect a relatively smoothly beveled annular zone of blending slope outwardly from said area of diopter-changing curvature correction.

13. Sculpture apparatus according to claim 8 or claim 9, in which the mask apertures are circularly annular and of progressively changing inner radius, and in which said mask apertures are of outer radius which when projected to the cornea via said zoom-lens system is greater than that of the maximum curvature-correcting area to be ablated, and a further circular mask aperture interposed between said controllable means and the location of beam delivery to the eye, said further mask aperture being of such radius as to limit beam delivery to the radius of said area of diopter-changing curvature correction.

14. The sculpture apparatus of claim 8 or claim 9, in which said controllable means includes shutter means operable to preclude laser-beam impingement at the cornea, said control means being operative to preclude laser-beam impingement at the cornea upon completion of beam exposure for each utilized mask aperture and for the period (1) of mask-indexing into the operative position of the next mask aperture in said progression and (2) of zoom-lens resetting for operative use of said next mask aperture.

15. Sculpture apparatus according to claim 8, in which said control means is connected to determine a different time of beam exposure and of zoom-lens utilization for operative use of each of a succession of mask apertures of said mask.

16. Sculpture apparatus according to claim 9, in which said control means is connected to determine a different number of pulses of beam exposure for each of a succession of apertures of said mask.

17. Sculpture apparatus for curvature-correcting operation upon the anterior surface of the cornea of an eye, said apparatus comprising laser means for producing a tissue-ablating output beam and controllable means for variably limiting the sectional area of said beam at impingement on the cornea, the area variation being over a range which at least includes a maximum curvature-correcting area to be ablated and being symmetrical with respect to a beam-projection axis which coincides with the optical axis of the eye, the intensity of laser-beam projection being limited per unit time to ablate but a fraction of a predetermined maximum depth of ablation into the stroma region of the cornea, said controllable means including (a) a zoom-lens system and (b) an indexible mask having a plurality of mask apertures of progressively changing area, and control means connected to said laser means and to said controllable means for so controlling zoom-lens setting for each of an indexed plurality of the apertures of said mask as to produce a relatively smooth variation of the sectional area of said beam at impingement on the cornea with an accompanying diopter change at the cornea, said relatively smooth variation being as compared with the stepped variation produced by use of the mask alone, said mask being one of a plurality of circular discs which are in axially separated array and which are so connected to said control means as to be separately indexible about the same axis of index rotation, each of said discs having a differently characterized progression of apertures of varying beam-transmitting sectional area, and one of the apertures of each disc having an opening area as to avoid beam-section limitation upon the beam-section-limiting ability of any aperture of any other disc of said plurality.

18. Sculpture apparatus for curvature-correcting operation upon the anterior surface of an eye, said apparatus comprising pulsing laser means for producing a succession of tissue-ablating pulses in an output beam and controllable means for variably limiting the sectional area of said beam at impingement on the cornea, the area variation being over a range which at least includes a maximum curvature-correcting area to be ablated and being symmetrical with respect to a beam-projection axis which coincides with the optical axis of the eye, the intensity of laser-beam projection being such that corneal-tissue ablation per pulse is but a fraction of desired maximum ablation into the stroma region of the cornea, said controllable means including (a) a zoom-lens system and (b) an indexible mask having a plurality of mask apertures of progressively changing area, and control means connected to said laser means and to said controllable means for so variably controlling zoom-lens setting for each of an indexed plurality of pulses in the course of zoom-lens variation for each of said indexed plurality of mask apertures whereby to achieve a relatively smooth variation of the sectional are of said beam at impingement on the cornea with an accompanying diopter change at the cornea, said relatively smooth variation being as compared with the stepped variation produced by use of the mask alone, said mask being one of a plurality of circular discs which are in axially separate array and which are so connected to said control means as to be separately indexible about the same axis of index rotation, each of said discs having a differently characterized progression of varying beam-transmitting sectional area, and one of the apertures of each disc having an opening of such sufficiently large beam-transmitting sectional area as to avoid beam-section limitation upon the beam-section-limiting ability of any aperture of any other disc of said plurality.

19. Sculpture apparatus according to claim 17 or claim 18, in which the mask apertures of at least one of said disc are circular and of progressively changing radius, whereby to effect a relatively smoothly profiled myopia-correcting diopter change.

20. Sculpture apparatus according to claim 17 or claim 18, in which the mask apertures of at least one of said discs are elongate rectangular and of progressively changing lateral width, and selectively operable means for orienting the elongation axes of said apertures in accordance with a predetermined orientation of desired astigmatism correction, whereby to effect a relatively smoothly profiled cylindrical diopter change.

21. Sculpture apparatus according to claim 17 or claim 18, in which the mask apertures of at least one of said discs are circularly annular and of progressively changing inner radius, and in which said mask apertures are of outer radius which when projected to the cornea via said zoom-lens system is greater than that of the maximum curvature-correcting area to be ablated, said controllable means further including continuously variable-iris means for varying said outer radius, said control means so coordinating iris aperture with zoom-lens setting and with the currently indexed mask aperture as to effect a relatively smoothly profiled hyperopia-correcting diopter change within said maximum curvature-correcting area and also to effect a relatively smoothly beveled annular zone of blending slope outwardly from said area of diopter-changing curvature correction.

22. Sculpture apparatus for curvature-generating operation upon the anterior surface of the cornea of an eye, said apparatus comprising laser means for producing a tissue-ablating output beam and controllable means for variably limiting the sectional area of said beam at impingement of the cornea, the area variation being over a range which at least includes a maximum optically used area to be ablated and being symmetrical with respect to a beam-projection axis which coincides with the optical axis of the eye, said controllable means including (a) a zoom-lens system and (b) at least one indexible mask having a plurality of mask apertures of progressively changing area, and control means connected to said laser means and to said controllable means for so controlling zoom-lens setting for each of an indexed plurality of apertures of said mask as to produce a relatively smooth variation of the sectional area of said beam at impingement of the cornea with an accompanying diopter change at the cornea, said relatively smooth variation being as compared with the stepped variation produced by use of the mask alone, the number of mask apertures and the relation of area change between one and the next mask aperture through the progression of area change being selected for limitation of requisite zoom-lens magnification to the range 1:2 of less, for each of the indexed positions of said mask, whereby the variation in energy density at the cornea is within the range 1:4.

23. Sculpture apparatus for curvature-correcting operation upon the anterior surface of the cornea of an eye, said apparatus comprising laser means for producing a tissue-ablating output beam and controllable means for variably limiting the sectional area of said beam at impingement on the cornea, the area variation being over a range which at least includes a maximum curvature-correcting data to be ablated and being symmetrical with respect to a beam-projection axis which coincides with the optical axis of the eye, the intensity of laser-beam projection being limited per unit time to ablate but a fraction of a predetermined maximum depth of ablation into the stroma region of the cornea, said controllable means including (a) a zoom-lens system and (b) an indexible mask having a plurality of mask openings of progressively changing area, and control means connected to said laser means and to said controllable means for so controlling zoom-lens setting for each of an indexed plurality of the openings of said mask as to produce a relatively smooth variation of the sectional area of said beam at impingement on the cornea with an accompanying diopter change at the cornea, said relatively smooth variation being as compared with the stepped variation produced by use of the mask alone, said controllable means further including means for varying the intensity of the laser beam, said last-mentioned means being so continuously coordinated with the control of zoom-lens setting as to compensate for flux-density dilution as a function of instantaneous zoom-lens magnification.

24. Sculpture apparatus for curvature-correcting operation upon the anterior surface of the cornea of an eye, said apparatus comprising pulsing laser means for producing a succession of tissue-ablating pulses in an output beam and controllable means for variably limiting the sectional area of said beam at impingement on the cornea, the area variation being over a range which at least includes a maximum curvature-correcting area to be ablated and being symmetrical with respect to a beam-projection axis which coincides with the optical axis of the eye, the intensity of laser-beam projection being such that corneal-tissue ablation per pulse is but a fraction of desired maximum ablation into the stroma region of the cornea, said controllable means including (a) a zoom-lens system and (b) an indexible mask having a plurality of mask openings of progressively changing area, and control means connected to said laser means and to said controllable means for so variably controlling zoom-lens setting for each of an indexed plurality of openings of said mask as to deliver a plurality of pulses in the course of zoom-lens variations for each of said indexed plurality of mask openings whereby to achieve a relatively smooth variation of the sectional area of said beam at impingement on the cornea with an accompanying diopter change at the cornea, said relatively smooth variation being as compared with the stepped variation produced by use of the mask alone, said controllable means further including means for varying the intensity of the laser beam, said last-mentioned means being so continuously coordinated with the control of zoom-lens setting as to compensate for flux-density dilution as a function of instantaneous zoom-lens magnification.

25. Sculpture apparatus according to claim 23 or claim 24, wherein said last-mentioned means includes a microprocessor having an intensity-control connection to said laser means and a magnification-control connection to said zoom-lens system.

26. Sculpture apparatus according to claim 23 or claim 24, wherein said last-mentioned means includes variable-density filter means interposed between said laser means and said zoom-lens system.

27. Sculpture apparatus according to claim 23 or claim 24, wherein said last-mentioned means includes variable-density filter means interposed between said laser means and said zoom-lens system, said variable-density filter means comprising two like variable-density filters in mutually opposite directions of varying density and coupled for opposing displacements through the laser beam in synchronism with variation of zoom-lens setting.

28. The method of using a tissue-ablating laser beam to remove a wound of stroma-penetrating depth from the anterior surface of a damaged cornea without net change in curvature of the optically used area of the cornea, said method comprising the steps of:
(a) determining the circular area that is both centered on the optical axis of the cornea and large enough to embrace both the superficial wound and the optically used area;
(b) removing epithelium from said circular area and smoothly filling the wound with substance having laser-ablatable response comparable with that of corneal tissue;
(c) performing a curvature-reducing procedure involving laser-beam exposure and control with varying radius of circular-spot delivery centered on the optical axis, wherein the radius varies throughout said circular area, and wherein depth of ablating penetration into the stroma on the optical axis is to a predetermined depth at least corresponding to that of the wound; and
(d) performing a curvature-increasing procedure involving laser-beam exposure and control with varying inner radius of annular-spot delivery centered on the optical axis, wherein the annular spot has an outer radius at least matching that of the procedure of step (c), and wherein the curvature increasing procedure is continued until it achieves maximum penetration to said predetermined depth.

29. The method of claim 28, in which the annular-spot delivery of the curvature-increasing procedure of step (d) involves varying outer radius which increases radially outwardly of the outer radius of the procedure of step (c).

30. The method of claim 28, in which the intensity distribution of beam projection to the optically used area exhibits a cross-sectional fall-off in the radially outward direction from said axis, and wherein the exposure time for the procedure of step (d) exceeds that for the procedure of step (c).

31. The method of claim 28, wherein said substance is epithelium tissue.

32. The method of using a tissue-ablating laser beam to remove a wound of stroma-penetrating depth from the anterior surface of a damaged cornea without net change in curvature of the optically used area of the cornea, said method comprising the steps of:
 (a) determining the circular area that is both centered on the optical axis of the cornea and large enough to embrace both the superficial wound and the optically used area;
 (b) removing epithelium from said circular area and smoothly filling the wound with substance having laser-ablatable response comparable with that of corneal tissue;
 (c) performing successive curvature-changing procedures involving laser-beam exposure and control with varying size of spot delivery centered on the optical axis, one of said procedures involving varying radius of circular-spot delivery and the other of said procedures involving varying inner radius of annular-spot delivery; and
 (d) the respective procedures of step (c) being of such relative duration as collectively to achieve at least said stroma-penetrating depth and to avoid a net change in curvature of the anterior surface of the cornea.

33. The method of using a tissue-ablating laser beam (i) to remove a wound of stroma-penetrating depth from the anterior surface of a damaged cornea which also requires curvature correction, and (ii) concurrently to effect a predetermined curvature correction in the optically used area of the cornea, said method comprising the steps of:
 (a) determining the circular area that is both centered on the optical axis of the cornea and large enough to embrace both the superficial wound and the optically used area;
 (b) removing epithelium from said circular area and smoothly filling the wound with substance having laser-ablatable response comparable with that of corneal tissue;
 (c) performing successive curvature-changing procedures involving laser-beam exposure and control with varying size of spot delivery centered on the optical axis, one of said procedures involving varying radius of circular-spot delivery and the other of said procedures involving varying inner radius of annular-spot delivery; and
 (d) the respective procedures of step (c) being of such predetermined relative duration as collectively to achieve at least said stroma penetrating depth and to achieve said predetermined curvature correction.

34. The method of claim 32 or claim 33, in which the annular-spot delivery procedure of step (c) involves varying outer radius which increases radially outwardly of the outer radius of the procedure of the circular-spot delivery procedure.

35. The method of claim 33, in which step (c) involves a further curvature-changing procedure involving varying width of elongate rectangular-spot delivery wherein the elongation extends diametrically through the optical axis and at angular orientation to effect an astigmatism correction.

36. The method of using a tissue-ablating laser beam to produce a uniform depth of penetration into the stroma of a cornea and over the optically used area of the cornea, wherein in the course of exposure sufficient to achieve said depth on a central axis of beam delivery, the intensity distribution of beam projection to said area exhibits substantially the same profile of fall-off in all radially outward directions from said axis, said method comprising the steps of:
 (a) delivering one exposure of said beam to said area with sufficiency to ablate the cornea to said depth on the central axis of beam delivery, whereby ablation depth is to progressively lesser extent as a function of radius outward from said axis, and
 (b) delivering another exposure of said beam to said area wherein the delivery is a circular annulus that is centered on said axis and wherein the inner radius of said annulus is a controlled variation of inner radius in the range which is outward to the limit of said area, the control of inner radius of said annulus being such in relation to the radial fall-off of beam intensity as to incrementally extend ablated-depth penetration from said lesser extent to said uniform depth.

37. The method of claim 26, wherein said area is a circle having a radius which is held constant throughout steps (a) and (b).

38. The method of claim 36, wherein in the course of performing steps (a) and (b) an annular area of the cornea adjacent to and radially outside said optically used area is subjected to tissue-ablating exposure which is annular and of progressively expanding radius.

39. The method of using a tissue-ablating laser beam both (1) to produce at least a predetermined depth of penetration into the stroma of a cornea and over the optically used area of the cornea, and (2) to effect a predetermined spherical-curvature correction in the cornea, wherein the intensity distribution of beam projection on a central axis of beam delivery to said area exhibits substantially the same profile of fall-off in all radially outward directions from said axis, and wherein the effect of beam exposure to said area to an extent sufficient for penetration to said depth is to produce a greater curvature reduction in the corneal profile of said area than is needed to effect said predetermined correction, said method comprising the steps of:
 (a) delivering a sufficient exposure of said beam to said area to ablate the cornea to said predetermined depth on the central axis of beam delivery, whereby to produce said greater curvature reduction in the corneal profile of said area, and
 (b) delivering another exposure to said area wherein the delivery is a circular annular that is centered on said axis and wherein the inner radius of said annulus is such a controlled variation of inner radius as to effect an increase in the curvature of said corneal profile to the extent of achieving said predetermined spherical-curvature correction.

40. The method of using a tissue-ablating laser beam both (1) to produce at least a predetermined depth of penetration into the stroma of a cornea and over the optically used area of the cornea, and (2) to effect a predetermined spherical-curvature correction in the cornea, wherein the intensity distribution of beam projection on a central axis of beam delivery to said area exhibits substantially the same profile of fall-off in all radially outward directions from said axis, and wherein the effect of beam exposure to said area to an extent sufficient for penetration to said depth is to produce a lesser curvature reduction in the corneal profile of said area than is needed to effect said predetermined correction, said method comprising the steps of:

(a) delivering a sufficient exposure of said beam to said area to ablate the cornea to said predetermined depth on the central axis of beam delivery, whereby to produce said lesser curvature reduction in the corneal profile of said area, and (b) delivering another exposure to said area wherein the delivery is a circular spot that is centered on said axis and wherein the radius of said spot is subjected to such controlled variation as to effect a decrease in the curvature of said corneal profile to the extent of achieving said predetermined spherical-curvature correction.

* * * * *